United States Patent [19]

Kanehira et al.

[11] Patent Number: 4,681,890

[45] Date of Patent: Jul. 21, 1987

[54] 3,4-DIHYDROBENZOPYRAN COMPOUNDS AND PHARMACEUTICAL COMPOSITION CONTAINING THE SAME

[75] Inventors: Koichi Kanehira; Manzo Shiono; Yoshiji Fujita; Takashi Nishida, all of Kurashiki; Johji Yamahara, Otsu, all of Japan

[73] Assignee: Kuraray Co., Ltd., Okayama, Japan

[21] Appl. No.: 790,670

[22] Filed: Oct. 23, 1985

[30] Foreign Application Priority Data

Oct. 30, 1984 [JP] Japan .................. 59-229367
Mar. 4, 1985 [JP] Japan .................. 60-43380

[51] Int. Cl.⁴ .................. C07D 405/12; A61K 31/455
[52] U.S. Cl. .................. 514/333; 514/337; 546/256; 546/269
[58] Field of Search .............. 546/269, 256; 514/333, 514/337

[56] References Cited

FOREIGN PATENT DOCUMENTS

| | | |
|---|---|---|
| 55-94382 | 7/1980 | Japan . |
| 56-18578 | 4/1981 | Japan . |
| 56-18579 | 4/1981 | Japan . |
| 56-145283 | 11/1981 | Japan . |
| 57-146768 | 9/1982 | Japan . |
| 57-158776 | 9/1982 | Japan . |
| 58-5168 | 1/1983 | Japan . |

OTHER PUBLICATIONS

Chemical Abstracts 94:30568z (1981).
Chemical Abstracts 98:4474d (1983).
Chemical Abstracts 86:161293p (1977).
Chemical Abstracts 86:133782d (1977).
Chemical Abstracts 88:11937d (1978).
Chemical Abstracts 96:19969b (1982).
Chemical Abstracts 97:216002c (1982).

Primary Examiner—Jane T. Fan

[57] ABSTRACT

Novel 3,4-dihydrobenzopyran compounds of the formula:

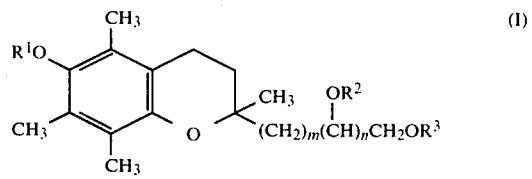

wherein $R^1$, $R^2$ and $R^3$ are each hydrogen or nicotinoyl group and at least one of them is nicotinoyl group, m is an integer of 0, 1 or 2, and n is an integer of 0 or 1, which is useful for prophylaxis and treatment of hyperlipemia and the compounds wherein $R^1$ and $R^3$ being nicotinoyl group and n is 0 being also effective for prophylaxis and treatment of hepatic diseases, and pharmaceutical composition containing said compounds as an active ingredient.

12 Claims, No Drawings

3,4-DIHYDROBENZOPYRAN COMPOUNDS AND PHARMACEUTICAL COMPOSITION CONTAINING THE SAME

This invention relates to novel 3,4-dihydrobenzopyran compounds and pharmaceutical compositions containing the same as an active ingredient. More particularly, it relates to 3,4-dihydrobenzopyran compounds of the formula:

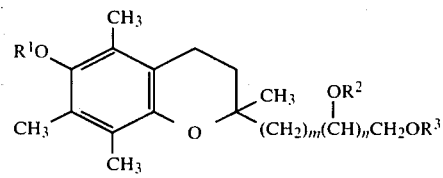

wherein $R^1$, $R^2$ and $R^3$ are each hydrogen or nicotinoyl group and at least one of them is nicotinoyl group, m is an integer of 0, 1 or 2, and n is an integer of 0 or 1, and a pharmaceutical composition containing the compound as an active ingredient, which is useful as an antilipemic agent. Moreover, it relates to a pharmaceutical composition for prophylaxis and treatment of hepatic diseases, which comprises as an active ingredient a compound of the formula:

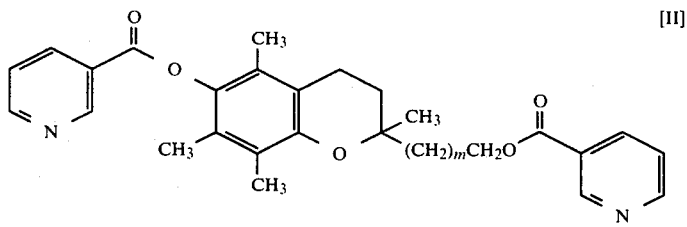

wherein m is as defined above.

PRIOR ART

There have been known some compounds which are somewhat similar to the compounds of this invention the chemical structure. For instance, Japanese Patent Publication (unexamined) No. 94382/1980 (Eisai) discloses a compound of the formula:

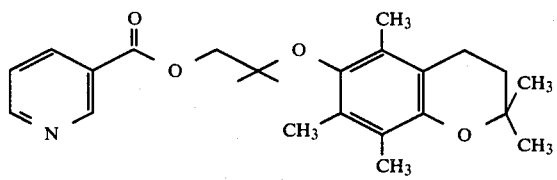

and mentions that the compound shows a cholesterol lowering activity. However, this compound is clearly distinguished from the compounds of this invention in chemical structure, i.e. in the substituent at 2-position of the benzopyran nucleus and also in the nicotinoyl ester substituent at 6-position.

Japanese Patent Publication (unexamined) No. 146768/1982 (=German Offenlegungsschrift No. 31 03 740) (BASF) discloses compounds of the formula:

$$[II]$$

wherein $R^5$ is a secondary or tertiary $C_{1-8}$ alkyl, $R^6$ is hydrogen or the same group as $R^5$, p is 1, 2 or 3, and q is 0, 1, 2 or 3. However, these compounds are clearly distinguished from the compounds of this invention in the substituent at 2-position of the benzopyran nucleus (not nicotinic ester residue), and further, this literature mentions that the compounds are useful as stabilizers for synthetic resins, this property being clearly different from the antilipemic activity and the anti-hepatic disease activity of the compounds of this invention.

As to antilipemic agents, it is known that when nicotinic acid is administered to a human, the blood cholesterol concentration is temporarily lowered, but the lowered concentration is not sustained. In regard to on agents showing sustained lowering of blood cholesterol concentration, some nicotinic acid esters, such as 2,2,6,6-tetrakis(nicotinoyloxymethyl)cyclohexanol (general name: Nicomol) and pentaerythritol tetranicotinate, have been proposed as antilipemic agents, and these compounds are clinically used. However, these nicotinic acid esters are not necessarily sufficient for lowering blood cholesterol.

Besides, it is known that liver has various functions, such as antidotal action, saccharometabolism, protein metabolism, lipid metabolism, production and secretion of bile, control of hormones, production of hemagglutinative substance: prothrombin, regeneration of hepatic cells, stock of various bio-elements (e.g. fats, glycogen, proteins, vitamins, etc.). These functions are acutely or chronically injured by various factors, such as alcohol, oligotrophy, virus, medicaments, toxic substances, bile duct obstruction, disorder of hepatic-circulation system, and the like. These injuries appear in varius symptoms, such as fatty liver, drug-induced hepatic diseases, alcoholic hepatitis, viral hepatitis, congestion of liver, cholestatic hepatic disease, jaundice, and finally liver cirrhosis. The mechanism of these hepatic diseases is not yet sufficiently clear.

In alcoholic hepatic disease which is recently on the increase, there is observed increase of lipid peroxides. From this viewpoint, for the treatment of alcoholic hepatic disease, there is used a medicament having antioxidation activity, such as glutathione, pantotheine, vitamin E in combination with rest cure and diet therapy. It is also reported that some malonic esters such as diisopropyl 1,3-dithiol-2-ylidene malonate and diisopropyl 1,3-dithiethan-2-ylidene malonate are useful as agents for the treatment of hepatic diseases (cf. Japanese Patent Publication Nos. 18578/1981, 18579/1981 and 5168/1983). However, these medicaments having antioxidation activity and other known compounds are not necessarily effective on the alcoholic and other hepatic diseases.

BRIEF DESCRIPTION OF THE INVENTION

An object of this invention is to provide novel 3,4-dihydrobenzopyran compounds useful as an antilipemic agent and/or an gent for prophylaxis and treatment of various hepatic diseases. Another object of the invention is to provide a pharmaceutical composition suitable for the prophylaxis and treatment of hyperlipemia which comprises the novel 3,4-dihydrobenzopyran compound of the formula [I] as an active ingredient. A further object of the invention is to provide a pharmaceutical composition for prophylaxis and treatment of various hepatic diseases which comprises the compound of the formula [II] as an active ingredient. These and other objects and advantages of the invention will be apparent to skilled person from the following description.

DETAILED DESCRIPTION OF THE INVENTION

The 3,4-dihydrobenzopyran compounds of the formula [I] include specifically the following compounds.

3,4-Dihydro-2-nicotinoyloxyethyl-2,5,7,8-tetramethyl-2H—benzopyran-6-ol
[Compound 1]:

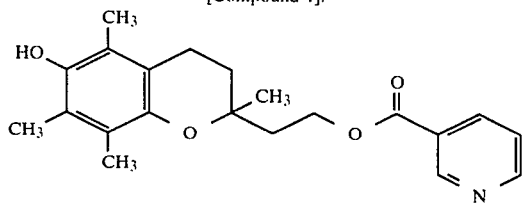

3,4-Dihydro-2-nicotinoyloxyethyl-2,5,7,8-tetramethyl-2H—benzopyran-6-yl nicotinate
[Compound 2]:

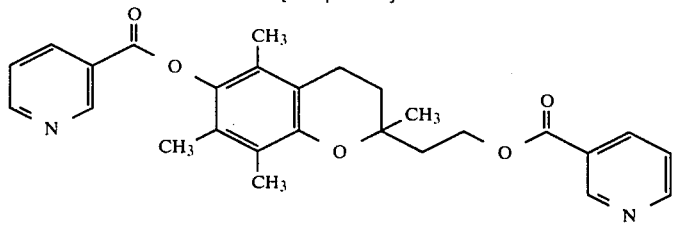

3,4-Dihydro-2-hydroxyethyl-2,5,7,8-tetramethyl-2H—benzopyran-6-yl nicotinate
[Compound 3]:

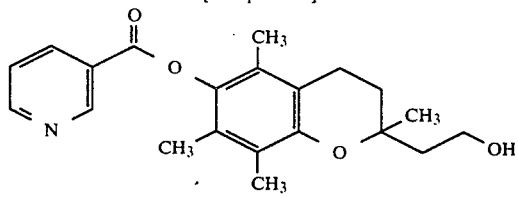

3,4-Dihydro-2-nicotinoyloxymethyl-2,5,7,8-tetramethyl-2H—benzopyran-6-ol
[Compound 4]:

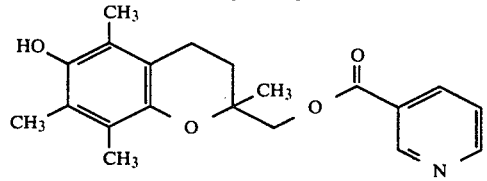

3,4-Dihydro-2-nicotinoyloxymethyl-2,5,7,8-tetramethyl-2H—benzopyran-6-yl nicotinate
[Compound 5]:

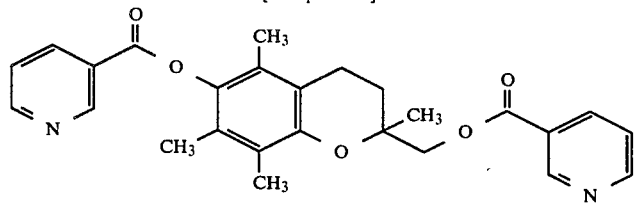

3,4-Dihydro-2-nicotinoyloxypropyl-2,5,7,8-tetramethyl-2H—benzopyran-6-yl nicotinate
[Compound 6]:

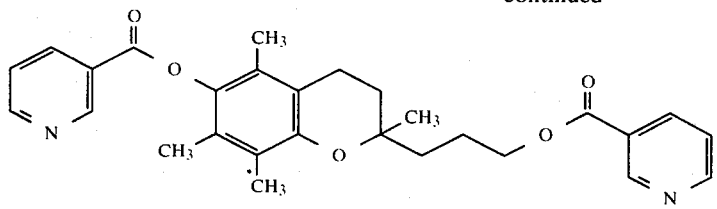

3,4-Dihydro-2-[2,3-di(nicotinoyloxy)propyl]-2,5,7,8-tetramethyl-2H—benzopyran-6-yl nicotinate [Compound 7]:

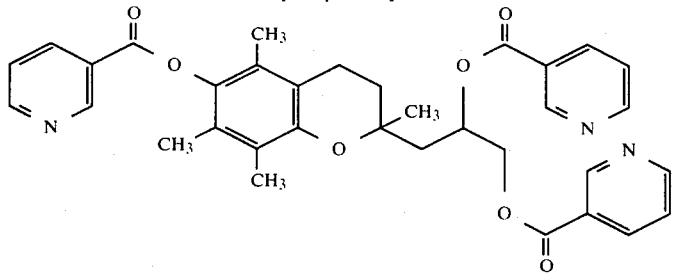

The compounds of the formula [II] useful for the prophylaxis and treatment of hepatic diseases include specifically the above-mentioned Compound 2, Compound 5 and Compound 6.

The 3,4-dihydrobenzopyran compounds of the formula [I] and [II] can be prepared by reacting a 3,4-dihydrobenzopyran-6-ol of the formula:

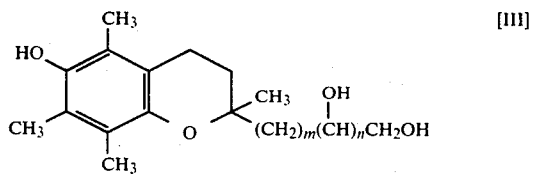

[III]

wherein m and n are as defined above, or a reactive derivative thereof with nicotinic acid or a reactive derivative thereof by a conventional esterification reaction. For example, 3,4-dihydrobenzopyran-6-ol of the formula [III] is reacted with a stoichiometric amount of nicotinoyl chloride hydrochloride in an inert solvent, such as hydrocarbons (e.g. toluene, benzene, hexane), halogenated hydrocarbons (e.g. carbon tetrachloride, dichloromethane, chloroform, dichloroethane, trichlene, etc.), ethers (e.g. diethyl ether, t-butyl methyl ether, diisopropyl ether, tetrahydrofuran, dimethoxyethane, etc.), ketones (e.g. acetone, methyl ethyl ketone, etc.), aprotic polar solvents (e.g. dimethylsulfoxide, dimethylformamide, etc.) or without any solvent. The reaction is carried out in the presence of a base, such as organic tertiary amines (e.g. pyridine, triethylamine, etc.) which is usually used in an amount of not less than 2.0 equimolar amount to the nicotinoyl chloride hydrochloride. The base may also be used as a solvent. The reaction is usually carried out at a temperature from room temperature to reflux temperature.

When an alkali metal salt of 3,4-dihydrobenzopyran-6-ol (a reactive derivative) is used, it is reacted with a stoichiometric amount of a reactive derivative of nicotinic acid, such as a nicotinoyl halide, nicotinic anhydride, a mixed anhydride of nicotinic acid and p-toluenesulfonic acid in an inert solvent as mentioned above at a temperature of from about −20° C. to reflux temperature.

The stoichiometric amount of nicotinic acid or its reactive derivative varies depending on the desired compound (i.e. mono-, di- or tri-nicotinate). For instance, when a mono-nicotinoyl compound is obtained, the nicotinic acid or its reactive derivative is used in an amount of 0.9-1.2 mole, preferably 1.0-1.1 mole, to 1 mole of 3,4-dihydrobenzopyran-6-ol or its reactive derivative. When a di- or tri-nicotinoyl compound is desired, the nicotinic acid or its reactive derivative is used in double or three times larger amount than the above, respectively.

The 3,4-dihydrobenzopyran compounds of the formula [I] and [II] thus prepared can be isolated and purified in a conventional manner. For example, the reaction mixture is poured into water, and the mixture is extracted with a solvent (e.g. diethyl ether, toluene, etc.). The extract is washed with aqueous sodium hydrogen carbonate and water, and after distilling off materials having a low boiling point, the resulting crude product is subjected to recrystallization and/or column chromatography on silica gel.

Among the starting 3,4-dihydrobenzopyran-6-ols of the formula [III], the compounds wherein n is 0 are known, and the compounds wherein n is 1 are novel. The novel compound of the formula [III] wherein n is 1 can be prepared by a conventional method as shown in the following reaction scheme:

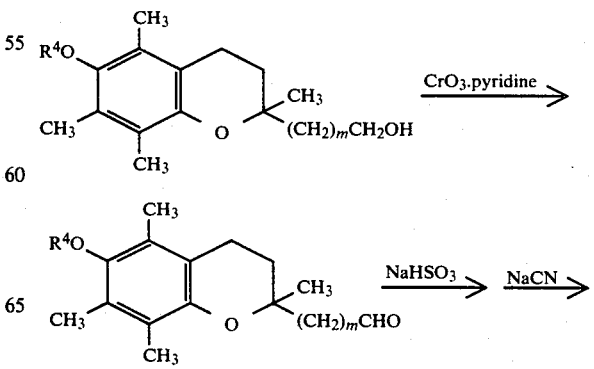

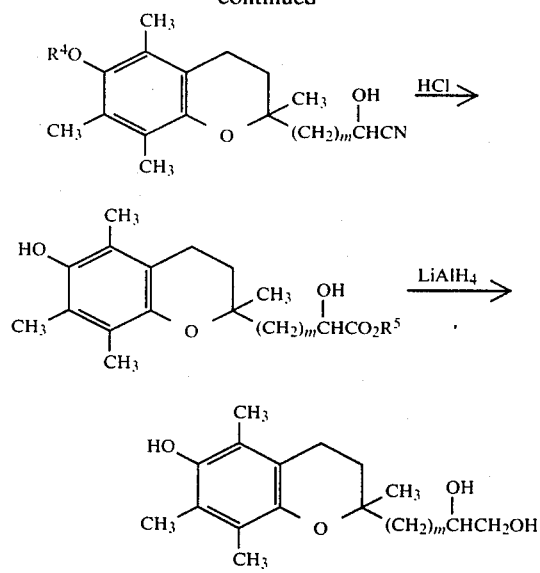

wherein m is as defined above, $R^4$ is a protecting group for hydroxy group, and $R^5$ is hydrogen atom or a lower alkyl group.

The pharmacological activities of the compounds [I] and [II] are illustrated by the following experiments.

(1) Blood Cholesterol Lowering Activity

Method dd-Male mice weighing about 25 g (one group: 10 mice) were allowed to fast for 12 hours, and thereto was orally administered a lipid emulsion (olive oil 32.7%, cholesterol 2.5%, sodium cholate 1.8%, sucrose 41.9%, and water 21.1%) in a dose of 25.5 ml/kg. A suspension of a test compound in gum arabic was orally administered to the mice twice, i.e. immediately after and 7 days after the administration of the lipid emulsion. 17 hours after the second administration of test compound, blood was collected from descending abdominal aorta under ether anesthesia. Total cholesterol in serum was measured by COD-p-chlorophenol colorimetry. As a reference compound, there was used Nicomol (chemical name: 2,2,6,6-tetrakis(nicotinoyloxymethyl)cyclohexanol) which is commercially available anticholesteremic agent.

Result

Serum cholesterol values at 17 hours after the second administration of test compound were compared with the serum cholesterol values in normal mice and hypercholesterolemic mice. The results are shown in Tables 1 to 4.

TABLE 1

| Test compound | Dose (mg/kg, p.o.) | Serum cholesterol value (mg/dl) |
|---|---|---|
| Normal mice | — | 98.6 ± 10.8 |
| Hypercholester-olemic mice | — | 172.2 ± 8.6* |
| Compound 1 | 355 | 130.7 ± 11.3 |
| Compound 4 | 341 | 159.4 ± 13.4 |
| Compound 5 | 452 | 127.9 ± 14.2 |
| Compound 6 | 474 | 123.8 ± 13.8 |
| Nicomol | 640 | 146.1 ± 14.7 |

TABLE 2

| Test compound | Dose (mg/kg, p.o.) | Serum cholesterol value (mg/dl) |
|---|---|---|
| Normal mice | — | 101.0 ± 5.8 |
| Hypercholester-olemic mice | — | 194.3 ± 9.5 |
| Compound 2 | 300 | 139.6 ± 9.3 |
| Nicomol | 640 | 139.4 ± 4.4 |

TABLE 3

| Test compound | Dose (mg/kg, p.o.) | Serum cholesterol value (mg/dl) |
|---|---|---|
| Normal mice | — | 109.1 ± 9.3 |
| Hypercholester-olemic mice | — | 164.0 ± 12.8 |
| Compound 7 | 571 | 143.6 ± 10.8 |
| Nicomol | 640 | 138.3 ± 12.5 |

TABLE 4

| Test compound | Dose (mg/kg, p.o.) | Serum cholesterol value (mg/dl) |
|---|---|---|
| Normal mice | — | 111.3 ± 8.6 |
| Hypercholester-olemic mice | — | 165.0 ± 13.4 |
| Compound 3 | 355 | 144.0 ± 10.5 |
| Nicomol | 640 | 142.7 ± 11.5 |

As is clear from Tables 1 to 4, all of the test compounds showed excellent blood cholesterol lowering activity. Particularly, Compounds 1, 2, 5 and 6 of the present invention showed about two times higher cholesterol lowering activity than Nicomol.

(2) Activity Against Alcoholic Hepatic Disease

Method dd-Male mice (4 weeks age, weighing about 15 g, one group: 10 mice) were fed with a hyperlipid feed [composition: cholesterol 1.0%, sodium cholate 0.5%, butter 5.0%, sucrose 30.0%, casein 10.0%, and M powder feed (manufactured by Oriental Yeast Co., Ltd., Japan) 53.5%] for 4 weeks. During the feeding, a suspension of a test compound in gum arabic and a 20% aqueous ethanol (15 ml/kg) were orally administered twice a day (morning and evening). After 4 weeks, mice were subjected to laparotomy under ether anesthesia, and blood was collected from the descending abdominal aorta. The blood thus collected was centrifuged at 3,000 r.p.m. for 15 minutes, and the enzymatic activity of ornithine carbamyl transferase (OCT) was measured with OCT-Test Wako (manufactured by Wako Pure Chemical Industries, Ltd., Japan).

Result

The OCT activity in serum of mice which were administered test compounds was compared with the OCT activity in serum of normal mice and in control mice which were administered only 20% aqueous ethanol. The results are shown in Table 5.

TABLE 5

| Test compound | Dose (mg/kg, p.o.) | OCT activity unit (mean ± S.E.) |
|---|---|---|
| Normal mice | — | 5.1 ± 3.2 |
| Ethanol-adminis-tered mice | — | 122.5 ± 17.0 |
| Compound 2 | 300 | 79.6 ± 12.2 |

As is clear from Table 5, the compound 2 of this invention showed excellent inhibition of increase of OCT activity which was induced by alcohol.

The activity against alcoholic hepatic disease of Compounds 5 and 6 was tested likewise. As the result, both compounds showed excellent inhibition of increase of OCT activity induced by alcohol in a similar degree to that of Compound 2.

(3) Activity Against Carbon Tetrachloride-Induced Hepatic Disease

Method

To dd male mice weighing 18–20 g (one group: 10 mice) was orally administered a suspension of a test compound in gum arabic twice or three times per day. On the third day, 1% carbon tetrachloride (v/v % in olive oil) was subcutaneously injected at the back of the mice in a dose of 2 ml/kg one hour after the last administration of test compound. 19 hours after the injection of $CCl_4$, a suspendion of a test compound in gum arabic was orally administerd. After one hour, the mice were subjected to laparotomy under ether anesthesia and blood was collected from the descending abdominal aorta. The blood thus collected was centrifuged at 3,000 r.p.m. for 15 minutes. The enzymatic activities of glutamic oxaloacetic transaminase (GOT) and glutamic pyruvic transaminase (GPT) in serum were measured with S.TA-Test Wako (manufactured by Wako Pure Chemical Industries, Ltd., Japan).

Result

The activities of GOT and GPT in serum of the mice which were administered test compounds were compared with the GOT and GPT activities in serum of normal mice and 1% $CCl_4$ (v/v % in olive oil)-administered mice. The results are shown in Table 6.

TABLE 6

| Test compound | Dose (mg/kg, p.o.) | GOT activity (average) | GPT activity (average) |
|---|---|---|---|
| Normal mice | — | 87.9 ± 5.3 | 74.0 ± 16.3 |
| $CCl_4$-administered mice | — | 914.3 ± 195.1 | 1251.4 ± 285.4 |
| Compound 2 | 300 | 582.9 ± 59.8 | 765.7 ± 84.4 |

As is clear from Table 6, the compound 2 of this invention showed excellent inhibition of increase of GOT and GPT activities induced by $CCl_4$.

The activity against $CCl_4$-induced hepatic disease of Compounds 5 and 6 was experimented likewise. As the result, both compounds showed excellent inhibition of increase of GOT and GPT activities induced by $CCl_4$ in a similar degree to that of Compound 2.

The compounds of this invention show a low toxicity. For instance, Compound 1 and Compound 2 have $LD_{50}$ of more than 5,000 mg/kg in mice (by oral administration).

The compounds of the formula [I] of this invention are useful for the prophylaxis and treatment of various diseases accompanied with arteriosclerosis, such as hypercholesteremia, hyperlipemia, atherosclerosis, cerebral circulation disorder, coronary insufficiency, and peripheral vascular disorder. Besides, the compounds of the formula [II] of this invention are also useful for the prophylaxis and treatment of various hepatic diseases, particularly hepatic diseases induced by chemicals such as alcohol and carbon tetrachloride, especially alcoholic hepatic disease. The compounds [II] are also effective against hepatic disorders accompanied with centrilobular or perilobular necrosis, hepatitis accompanied with intralobular sporadic necrosis and mesenchymal reaction, fatty liver, liver cirrhosis, or congestion of liver, and have further various pharmacological activities, such as, promoting of secretion of bile and bile acid (i.e. cholagogic activity), lowering of alcoholic level in blood, lowering of abnormally high sugar level in blood, relaxation of metallic toxication, and the like. Thus, the compounds [II] of this invention are effective by various factors and hence are useful for the treatment of acute or chronic hepatic diseases in human or in other animals, for instance, fatty liver, alcoholic hepatitis, hepatitis, drug-induced hepatic diseases, congestion of liver, cholestatic hepatic disease, and final symptom thereof, i.e. liver cirrhosis. Besides, according to histopathological finding, the compounds [II] are also effective on hepatic disease caused by hepatic necrosis, and hence, these compounds are also useful for the treatment of hepatic diseases accompanied with such necrosis in human or in other animals. Since the compounds [II] can also enhance the functions of liver, such as secretion of bile and bile acid, saccharometabolism, detoxication of toxic substances (e.g. alcohols), they are also useful as cholagogic agents and agents for jaundice in human or in other animals. Furthermore, since the compounds [II] can lower the blood sugar level, they are useful as antidiabetic drugs in human or in other animals. Besides, these compounds are also useful as blood alcohol level lowering agents or as an antidote, and hence, are effective for the treatment of alcoholic intoxication and the morning after in humans.

In the use of the compounds of this invention for the prophylaxis and treatment of various hepatic diseases as mentioned above, the dosage may vary widely depending on the routes of administration, the conditions, body weight, age and sex of the patient, the judgement of a physician who treats the patient, etc., but is usually in the range of 50 to 1,000 mg/day, preferably 100 to 500 mg/day, for oral administration, either at a time or in several divided portions daily.

The compounds of this invention may be administered by oral route or by parenteral route, but preferably by oral route.

The compounds of this invention may be formulated into pharmaceutical compositions or agents using conventional pharmaceutically acceptable, solid or liquid carriers or diluents in the usual manner.

The pharmaceutical composition or agent of this invention is preferably prepared in the form suitable for absorption from the alimentary canal. For oral administration, the compounds of this invention may be formulated into the conventional forms, for example, solid preparations such as tablets, pills, powders, capsules, granules, or fine granules. The preparations for oral administration can be prepared by admixing the active compound with conventional carriers or diluents, such as binding agents (e.g. syrup, gum arabic, gelatin, sorbitol, tragacanth gum, polyvinylpyrrolidone, etc.), excipients (e.g. lactose, corn starch, calcium phosphate, sorbitol, glycine, etc.), lubricants (e.g. magnesium stearate, talc, polyethylene glycol, silica, etc.), disintegrators (e.g. potato starch, etc.), wetting agents (e.g. sodium laurylsulfate, etc.). The tablets may also be coated by conventional coating agents. The preparations for oral administration include also liquid preparations, such as aqueous or oily suspensions, solutions, syrups, elixirs, and the like. The preparations may be in a dried state which is re-dissolved in water or other suitable vehicles when used. The liquid preparations can be prepared by dissolving or suspending the active compound in conventional carriers or diluents, for example, suspension medium (e.g. sorbitol syrup, methyl cellulose, glucose/sugar syrup, gelatin, hydroxyethyl cellulose, carboxymethyl cellulose, aluminum stearate gel, hardened food oil, etc.), emulsifying agents (e.g. lecithin, sorbitan monooleate, gum arabic, etc.), non-aqueous vehicles (e.g. almond oil, fractionated coconut oil, oily esters, propylene glycol, ethyl alcohol, etc.), preservatives (e.g. methyl p-hydroxybenzoate, propyl p-hydroxybenzoate, sorbic acid, etc.), and the like.

The pharmaceutical composition or agent of this invention may optionally further contain other conventional additives, such as coloring agents, flavors, coreagents, antiseptics, solubilizers, suspending agents and dispersing agents.

The pharmaceutical composition or agent may be in unit dosage forms such as tablets, capsules, coated tablets and ampoules as mentioned above, or may be in a form contained in a multiunit dosage receptacle.

The pharmaceutical composition or agent of this invention usually contains the active compound of this invention in a concentration of 0.01 to 50% by weight, preferably 0.1 to 20% by weight, based on the whole weight of the composition or agent, while the concentration may vary depending on the dosage forms and the like.

The compounds of this invention, the process for preparation thereof and pharmaceutical compositions are illustrated by the following Examples and Preparations, but should not be construed to be limited thereto.

EXAMPLE 1

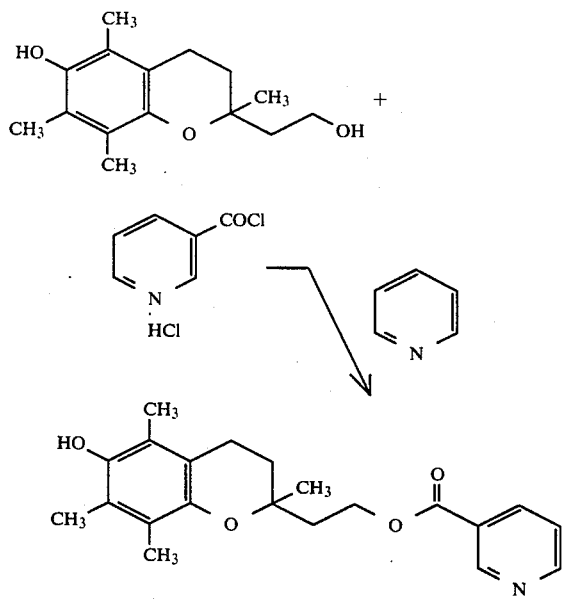

To a mixture of 3,4-dihydro-2-hydroxyethyl-2,5,7,8-tetramethyl-2H-benzopyran-6-ol (8 g), pyridine (5.06 g) and 1,2-dichloroethane (64 ml) is added nicotinoyl chloride hydrochloride (5.7 g) under nitrogen gas, and the mixture is refluxed. Nicotinoyl chloride hydrochloride (1.14 g) and pyridine (1.01 g) are further added, and the mixture is continuously refluxed until the starting materials disappear, by which the reaction is completed. The reaction mixture is cooled and then poured into ice water, and the mixture is washed with aqueous sodium hydrogen carbonate and dried over anhydrous magnesium sulfate. After distilling off materials having a low boiling point, the residue is separated and purified by column chromatography on silica gel to give 3,4-dihydro-2-nicotinoyloxyethyl-2,5,7,8-tetramethyl-2H-benzopyran-6-ol (Compound 1) (9.0 g, yield 79.2%) having the following properties.

$^1$H-NMR spectrum (90 MHz) $\delta_{HMS}^{CDCl_3}$: 1.33 (s, 3H), 1.7–2.25 (m, 13H), 2.61 (t, J=7 Hz), 2H), 4.53 (dt, J=2 Hz and 7 Hz, 2H), 4.98 (broad s, 1H), 7.33 (dd, J=5 Hz and 8 Hz, 1H), 8.26 (ddd, J=2 Hz, 2 Hz and 8 Hz, 1H), 8.73 (dd, J=2 Hz and 5 Hz, 1H), 9.17 (d, J=2 Hz, 1H).

FD-Mass spectrum: [M+] 355.

EXAMPLE 2

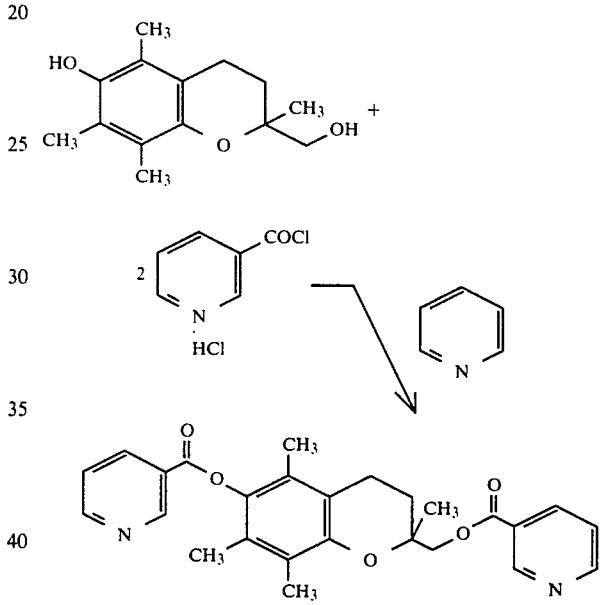

To a mixture of 3,4-dihydro-2-hydroxymethyl-2,5,7,8-tetramethyl-2H-benzopyran-6-ol (4 g, 16.9 mmole), pyridine (5.9 g) and 1,2-dichloroethane (70 ml) is added nicotinoyl chloride hydrochloride (6.64 g) under nitrogen gas, and the mixture is refluxed. After completion of the reaction, the reaction mixture is cooled and then poured into ice water, and the mixture is washed with aqueous sodium hydrogen carbonate and dried over anhydrous magnesium sulfate. After distilling off materials having a low boiling point, the residue is separated and purified by column chromatography on silica gel to give 3,4-dihydro-2-nicotinoyloxymethyl-2,5,7,8-tetramethyl-2H-benzopyran-6-yl nicotinate (Compound 5) (6.9 g, yield 91.5%) having the following properties.

$^1$H-NMR spectrum (90 MHz) $\delta_{HMS}^{CDCl_3}$: 1.37 (s, 3H), 1.98 (s, 3H), 2.01 (s, 3H), 2.07 (s, 3H), 1.8–2.1 (m, 2H), 2.66 (t, J=7 Hz, 2H), 4.25–4.6 (m, 2H), 7.25–7.55 (m, 2H), 8.27 (ddd, J=2 Hz, 2 Hz and 8 Hz, 1H), 8.47 (ddd, J=2 Hz, 2 Hz and 8 Hz, 1H), 8.77 (dd, J=2 Hz and 5 Hz, 1H), 8.81 (dd, J=2 Hz and 5 Hz, 1H), 9.25 (d, J=2 Hz, 1H), 9.44 (d, J=2 Hz, 1H).

FD-Mass spectrum: [M+] 446.

EXAMPLES 3 AND 4

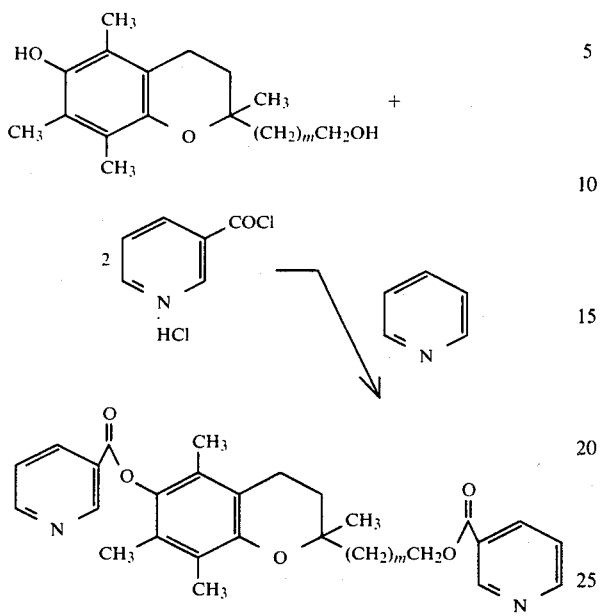

In the same manner as described in Example 2 except that 3,4-dihydro-2-hydroxyethyl-2,5,7,8-tetramethyl-2H-benzopyran-6-ol or 3,4-dihydro-2-hydroxypropyl-2,5,7,8-tetramethyl-2H-benzopyran-6-ol (16.9 mmole respectively) is used instead of 3,4-dihydro-2-hydroxymethyl-2,5,7,8-tetramethyl-2H-benzopyran-6-ol (16.9 mmole), the reaction and the isolation of the products are carried out to give the corresponding 3,4-dihydro-2-nicotinoyloxyethyl-2,5,7,8-tetramethyl-2H-benzopyran-6-yl nicotinate (Compound 2) and 3,4-dihydro-2-nicotinoyloxypropyl-2,5,7,8-tetramethyl-2H-benzopyran-6-yl nicotinate (Compound 6), respectively. The yield and properties of these compounds are shown in the following Table 7.

TABLE 7

| Product | Yield(%) | Properties |
|---|---|---|
| Compd. 2 | 62.8 | $^1$H—NMR spectrum (90 MHz) $\delta_{HMS}^{CDCl_3}$: 1.34 (s, 3H), 2.00 (s, 6H), 2.06 (s, 3H), 1.70–2.20 (m, 4H), 2.62 (t, J=7 Hz, 2H), 4.52 (dt, J=2 Hz and 7 Hz, 2H), 7.32 (dd, J=5 Hz and 8 Hz, 1H), 7.42 (dd, J=5 Hz and 8 Hz, 1H), 8.21 (ddd, J=2 Hz, 2 Hz and 8 Hz, 1H), 8.34 (ddd, J=2 Hz, 2 Hz and 8 Hz, 1H), 8.73 (dd, J=2 Hz and 5 Hz, 1H), 8.83 (dd, J=2 Hz and 5 Hz, 1H), 9.18 (d, J=2 Hz, 1H) 9.41 (J=2 Hz, 1H) FD-Mass spectrum: [M$^+$] 460 |
| Compd. 6 | 68.1 | $^1$H—NMR spectrum (90 MHz) $\delta_{HMS}^{CDCl_3}$: 1.25 (s, 3H), 1.96 (s, 3H), 1.99 (s, 3H), 2.09 (s, 3H), 1.5–2.3 (m, 15H), 2.59 (t, J=7 Hz, 2H), 4.2–4.5 (m 2H), 7.33 (dd, J=5 Hz and 8 Hz, 1H), 7.43 (dd, J=5 Hz and 8 Hz, 1H), 8.05–8.35 (m, 1H), 8.46 (ddd, J=2 Hz, 2 Hz and 8 Hz, 1H), 8.74 (dd, J=2 Hz and 5 Hz, 1H), 8.83 (dd, J=2 Hz and 5 Hz, 1H), 9.20 (m 1H), 9.47 (m 1H) FD-Mass spectrum: [M$^+$] 474 |

EXAMPLES 5 TO 7

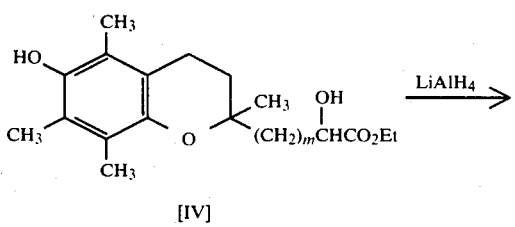

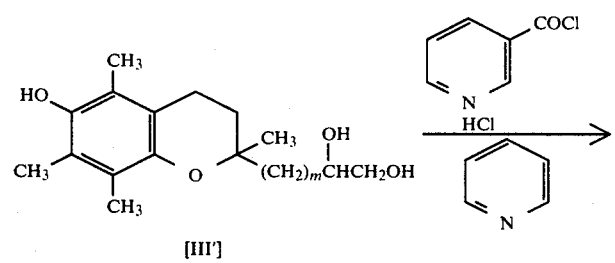

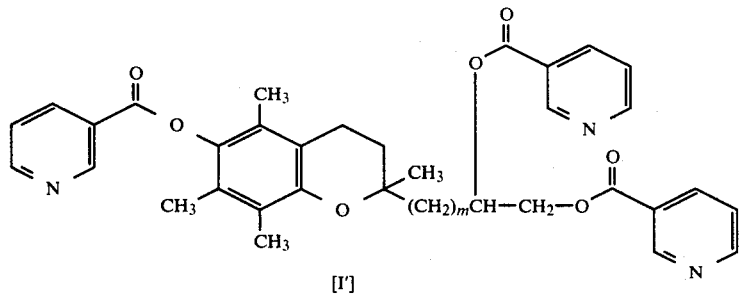

To a mixture of lithium aluminum hydride (1.77 g) and tetrahydrofuran (200 ml) is added dropwise a mixture of an ester (IV) (32 mmole) and tetrahydrofuran (90 ml) at a reflux temperature under nitrogen gas. After the addition, the mixture is refluxed for one hour. The reaction mixture is cooled and then poured into ice-water. To the mixture is added diluted hydrochloric acid, and the mixture is extracted with diethyl ether. The extract is washed with saturated aqueous sodium chloride solution and dried over anhydrous sodium sulfate. After distilling off materials having a low boiling point, the resulting residue is separated and purified by column chromatography on silica gel to give the corresponding 3,4-dihydrobenzopuran-6-ol [III']. The yield and FD-Mass spectrum thereof are shown in Table 8.

TABLE 8

| Ex. No. | 3,4-Dihydrobenzo-pyran-6-ol [III'] | Yield (%) | FD-Mass spectrum |
|---|---|---|---|
| 5 | n = 0 | 41 | [M+] 266 |
| 6 | n = 1 | 36 | [M+] 280 |
| 7 | n = 2 | 73 | [M+] 294 |

To a mixture of the 3,4-dihydrobenzopyran-6-ol [III'] obtained above (10.8 mmole), pyridine (6.19 g) and 1,2-dichloroethane (100 ml) is added nicotinoyl chloride hydrochloride (6.94 g), and the mixture is refluxed until the reaction is completed. The reaction mixture is cooled and poured into ice-water. The mixture is washed with aqueous sodium hydrogen carbonate solution and dried over anhydrous magnesium sulfate. After distilling off materials having a low boiling point, the resulting residue is separated and purified by column chromatography on silica gel to give the corresponding nicotinates [I'], respectively. The results are shown in Table 9.

TABLE 9

| Ex. No. | Nicotinate [I'] | Yield (%) | FD-Mass spectrum |
|---|---|---|---|
| 5 | n = 0 | 60 | [M+] 581 |
| 6 | n = 1 | 61 | [M+] 595 |
| 7 | n = 2 | 82 | [M+] 609 |

EXAMPLES 8 TO 10

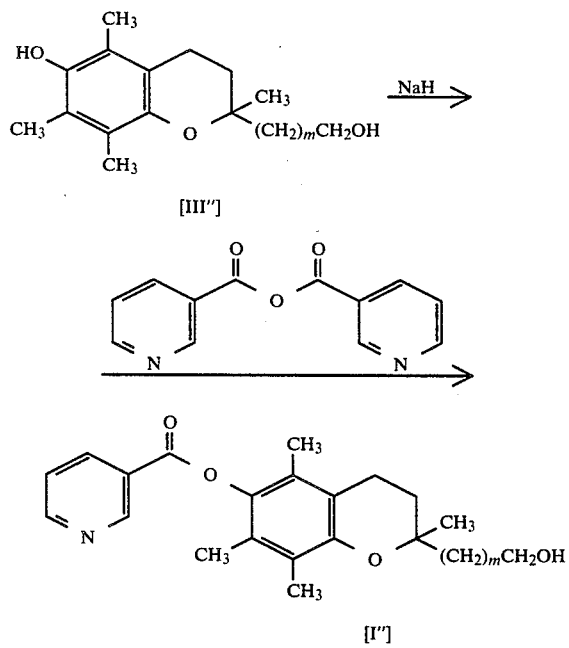

To a mixture of 3,4-dihydrobenzopyran-6-ol [III''] (10 mmole) and N,N-dimethylformamide (100 mmole) is added sodium hydride (10 mmole) to prepare the corresponding sodium phenoxide solution. The above sodium phenoxide solution is added dropwise to a solution of nicotinic anhydride (10 mmole) in N,N-dimethylformamide (50 ml) and the mixture is stirred. The reaction mixture is poured into diluted hydrochloric acid, and the mixture is extracted with diethyl ether. The extract is washed with water, aqueous sodium hydrogen carbonate solution and saturated aqueous sodium chloride solution in this order, and dried over anhydrous sodium sulfate. The materials having a low boiling point are distilled off. The resulting residue is separated and purified by column chromatography on silica gel to give the corresponding nicotinates [I'']. The results are shown in Table 10.

TABLE 10

| Ex. No. | Nicotinate [I''] | Yield (%) | FD-Mass spectrum |
|---|---|---|---|
| 8 | n = 0 | 71 | [M+] 341 |
| 9 | n = 1 | 75 | [M+] 355 |
| 10 | n = 2 | 70 | [M+] 369 |

The following Preparations are examples of compositions wherein 3,4-dihydro-2-nicotinoyloxyethyl-2,5,7,8-tetramethyl-2H-benzopyran-6-yl nicotinate (Compound 2) of this invention is contained as an active ingredient.

| Preparation 1 [Tablets] | |
|---|---|
| Compound 2 of this invention | 100 g |
| Corn starch | 145 g |
| Carboxymethyl cellulose | 40 g |
| Polyvinylpyrrolidone | 9 g |
| Calcium stearate | 6 g |
| Total | 300 g |

In accordance with the above formulation, tablets (one tablet: 300 mg) are prepared in a conventional manner. The Compound 2 of this invention is contained in an amount of 100 mg per each tablet.

| Preparation 2 [Powders and Capsules] | |
|---|---|
| Compound 2 of this invention | 100 g |
| Crystalline cellulose | 200 g |
| Total | 300 g |

Both powders as above are mixed to give powders. The powders are packed in No. 3 hard capsules to give capsules.

What is claimed is:

1. A 3,4-dihydrobenzopyran compound of the formula:

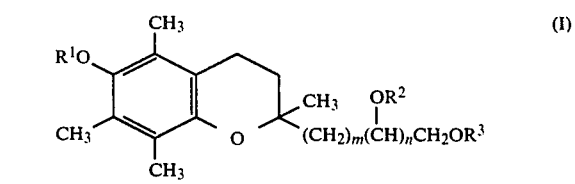

wherein $R^1$, $R^2$ and $R^3$ are each hydrogen or nicotinoyl group and at least one of them is nicotinoyl group, m is an integer of 0, 1 or 2, and n is an integer of 0 or 1.

2. The compound as claimed in claim 1, which is 3,4-dihydro-2-nicotinoyloxyethyl-2,5,7,8-tetramethyl-2H-benzopyran-6-ol.

3. The compound as claimed in claim 1, which is 3,4-dihydro-2-nicotinoyloxyethyl-2,5,7,8-tetramethyl-2H-benzopyran-6-yl nicotinate.

4. The compound as claimed in claim 1, which is 3,4-dihydro-2-hydroxyethyl-2,5,7,8-tetramethyl-2H-benzopyran-6-yl nicotinate.

5. The compound as claimed in claim 1, which is 3,4-dihydro-2-nicotinoyloxymethyl-2,5,7,8-tetramethyl-2H-benzopyran-6-ol.

6. The compound as claimed in claim 1, which is 3,4-dihydro-2-nicotinoyloxymethyl-2,5,7,8-tetramethyl-2H-benzopyran-6-yl nicotinate.

7. The compound as claimed in claim 1, which is 3,4-dihydro-2-nicotinoyloxypropyl-2,5,7,8-tetramethyl-2H-benzopyran-6-yl nicotinate.

8. The compound as claimed in claim 1, which is 3,4-dihydro-2-[2,3-di(nicotinoyloxy)propyl]-2,5,7,8-tetramethyl-2H-benzopyran-6-yl nicotinate.

9. A pharmaceutical composition for the prophylaxis and treatment of hyperlipemia which comprises as an active ingredient a prophylactically or therapeutically effective amount of a 3,4-dihydrobenzopyran compound of the formula:

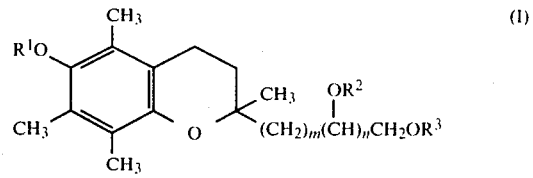

wherein $R^1$, $R^2$ and $R^3$ are each hydrogen or nicotinoyl group and at least one of them is nicotinoyl group, m is an integer of 0, 1 or 2, and n is an integer of 0 or 1, in admixture with a pharmaceutically acceptable carrier or diluent.

10. A pharmaceutical composition for the prophylaxis and treatment of hepatic diseases, which comprises as an active ingredient a prophylactically or therapeutically effective amount of a 3,4-dihydrobenzopyran compound of the formula:

(II)

wherein m is an integer of 0, 1 or 2, in admixture with a pharmaceutically acceptable carrier or diluent.

11. A method for the prophylaxis or treatment of hyperlipemia which comprises administering to an animal susceptible to or suffering from hyperlipemia a prophylactically or therapeutically effective amount of 3,4-dihydrobenzopyran compound as defined in claim 1.

12. A method for the prophylaxis or treatment of hepatic diseases, which comprises administering to a human or other animal susceptible to or suffering from hepatic disease a prophylactically or therapeutically effective amount of a 3,4-dihydrobenzopyran of the formula:

(II)

wherein m is an integer of 0, 1 or 2.